US006495317B1

(12) United States Patent
Loescher et al.

(10) Patent No.: US 6,495,317 B1
(45) Date of Patent: Dec. 17, 2002

(54) DNA ENCODINGMANNOSE 6-PHOSPHATE REDUCTASE AND RECOMBINANTS PRODUCED THEREFROM

(75) Inventors: Wayne H. Loescher, Okemos, MI (US); John D. Everard, East Lansing, MI (US); Rebecca Grumet, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/166,438

(22) Filed: Oct. 5, 1998

Related U.S. Application Data

(62) Division of application No. 08/731,320, filed on Oct. 15, 1996, now Pat. No. 6,416,985.

(51) Int. Cl.$^7$ ................................................. C12Q 1/68
(52) U.S. Cl. ........................................ 435/6; 536/23.2
(58) Field of Search ............................ 435/6, 189, 190; 536/23.2, 23.6

(56) References Cited

U.S. PATENT DOCUMENTS

| | | | |
|---|---|---|---|
| 5,128,256 A | 7/1992 | Huse et al. | 435/172.3 |
| 5,268,288 A | 12/1993 | Pharr | 435/190 |
| 5,492,820 A | 2/1996 | Sonnewald et al. | 435/69.1 |

OTHER PUBLICATIONS

Evarard et al. "Cloning of mannose 6–phosphate reductase fro celery" HortScience, vol. 30 (4), p. 898, abstract number 829, Jul. 1995.*
Everard et al. "Molecular cloning of mannose–6–phosphate reductase and its developmental expression in celery" Plant Physiol. 113, 1427–1435, 1997.*
Bieleski, R.L., Sugar alcohols. In: F.A. Loewus and W. Tanner, eds., Plant Carbohydrates I. Intracellular Car. Encyc. Plant. Physiol. vol. 13A, New Series, Springer–Verlag, NY, pp. 158–192 (1982).
Bohnert, Hans J., et al., The Plant Cell, 7:1099–1111 (1995).
Ahmad, I., et al., New Phytol. 82:671–679 (1979).
Hirai, M., Plant Cell Physiol. 24:925–931 (1983).
Everard et al., Plant Physiol. 102:345–356 (1993).
Stoop, J.M.H., et al., Plant Physiol. 106:503–511 (1994).
Kanayama, Y., et al., Plant Physiology 100:1607–1608 (1992).
Williamson, J.S., et al., Proc. Natl. Acad. Sci 92:7148–7152 (1995).
Tarczynski, M.C., et al., Science 259:508–510 (1993).
Thomas, J. C., et al., Plant Cell and Environ. 18:801–806 (1995).
Tao, R., et al., Plant Cell Physiol 36:525–532 (1995).
Hunkerpillar et al., Methods in Enzymology 91:227–236 (1983).
Pharr, D.M., et al., Plant Physiol. 180–194 (1995).
Loescher, W.H., et al., Plant Physiol. 170–178 (1995).
Bartels, D., et al., EMBO J 10:1037–1043 (1991).
Rumpho, M.E., et al., Plant Physiol. 73:869–873 (1983).
Harloff, H.J., et al., J. Plant Physiol. 141:513–520 (1993).
Loescher, W.H., et al., Plant Physiol. 98: 1396–1402 (1992).
Gilmour, S.J., et al., Plant Physiol. 87:745–750 (1988).
Hondred, D., et al., Plant Mol. Biol., 9:259–275 (1987).
Ried, J.K., et al., BioTechniques 12:660–666 (1992).
Bradford, M.M., Anal. Biochem. 136:248–254 (1976).
Bohren et al., J. Biol. Chem. 264:9547–9551 (1989).
Borhani, D.W., et al., J. Biol. Chem. 267:24841–24847 (1992).
Morijana et al., FASEB J 46:1330 (Abstract) (1987).
Schade et al., J.B.C. 265(7) : 3628–3635 (1990).
Petrash et al., JBC 267 (34) : 24833–24840 (1992).
Anderson et al., Planta 196:118–124 (1995).
Laemmli, U.K., Nature vol. 227 680–685 (1970).
Loescher, W.H., Physiol. Plantarum 70:553–557 (1987).
Fox, T.C., et al Plant Physiology 82:307–311 (1986).
Flora and Madore Planta 189:484–490 (1993).
Loescher, W.H. and Everard, J.D., Photoassimilate Distribution in Plants and Crops, 185–207 (1996).
Davis, J.M., et al., Plant Physiol, 86:129–133 (1988).
Everard, J.D., et al., Plant Physiol., 106:281–292 (1994).
Escobar–Gutierrez, A., et al., Plant Physiol. Supp 105: Abstract 575 (1994).
Quick, W.P. and Schaffer, A.A., Sucrose metabolism in sources and sinks. In: Photoassimilate distribution inplants and crops: source–sink relationships. Zamski, E., and Schaffer A., (eds) Marcel Dekker, Inc.: pp. 115–156 (1996).
Preiss, J. and Sivak, M.N., Starch synthesis in sinks and sources. In: Photoassimilate distribution in plants and crops: source–sink relationships. Zamski, E., and Schaffer A., (eds), Marcel Dekker, Inc.: pp. 63–96 (1996).

* cited by examiner

*Primary Examiner*—Nashaat T. Nashed
(74) *Attorney, Agent, or Firm*—Ian C. McLeod

(57) ABSTRACT

DNA encoding mannose 6-phosphate reductase (M6PR) and the use of the DNA in vectors and bacteria and in plants. The enzyme enables the production of mannitol in plants which increases stress tolerance, particularly to salt.

5 Claims, 7 Drawing Sheets

```
    M . . V T L S S G . . M P V L G L G V W R L D K . E L K . V  Functional similarity 1   M S T V T L S S G Y E M P V I G L G L W R L E K D E L K E V  A6PR protein aa
1   M A - I T L N S G F K M P V L G L G V W R M D R N E I K N L  M6PR ORF 29 Dec 95

L L S A I . L G Y R H F D C A A . Y K S E A D V G E A L . E  Functional similarity 31  I L N A I K I G Y R H F D C A A H Y K S E A D V G E A L A E  A6PR protein aa
30  L L S A I N L G Y R H F D C A A D Y K N E L E V G E A F K E  M6PR ORF 29 Dec 95

A F . T . L V K R E D L F I T T K L W N S D H G H V V E A C  Functional similarity 61  A F K T G L V K R E E L F I T T K I W N S D H G H V V E A C  A6PR protein aa
60  A F D T D L V K R E D L F I T T K L W N S D H G H V I E A C  M6PR ORF 29 Dec 95

K N S L . K L Q L D Y L D L Y L V H . P M A S K H S . I G .  Functional similarity 91  K N S L E K L Q I D Y L D L Y L V H Y P M P T K H N A I G K  A6PR protein aa
90  K N S L K K L Q L E Y L D L Y L I H F P M A S K H S G I G T  M6PR ORF 29 Dec 95

T . S L L . D D . V L D V D A T I S L . . T W . . M E K . V  Functional similarity 121 T A S L L G E D K V L D I D V T I S L Q Q T W E G M E K T V  A6PR protein aa
120 T R S I L D D E G V W E V D A T I S L E A T W H E M E K L V  M6PR ORF 29 Dec 95

. L G L V R S I G L S N Y D V . L T R D . L . Y S K I K P A  Functional similarity 151 S L G L V R S I G L S N Y E L F L T R D C L A Y S K I K P A  A6PR protein aa
150 E M G L V R S I G I S N Y D V Y L T R D I L S Y S K I K P A  M6PR ORF 29 Dec 95

V S Q I E T H P Y F Q R D S L V K F C . K . G V A I T A H T  Functional similarity 181 V S Q F E T H P Y F Q R D S L V K F C M K H G V L P T A H T  A6PR protein aa
180 V N Q I E T H P Y F Q R D S L I K F C Q K Y G I A I T A H T  M6PR ORF 29 Dec 95
```

FIG. 4A

```
          P L G G A A A N . D . F G S V S . L D D P V L . . V . . K .   Functional similarity
211       P L G G A A A N K D M F G S V S P L D D P V L N D V A K K Y   A6PR protein aa
210       P L G G A L A N T E R F G S V S C L D D P V L K K L S D K H   M6PR ORF 29 Dec 95

G K S V A Q I . L R W G V Q R . T A V I P K S S K . . R L .   Functional similarity
241       G K S V A Q I C L R W G I Q R K T A V I P K S S K I Q R L K   A6PR protein aa
240       N K S P A Q I V L R W G V Q R N T I V I P K S S K T K R L E   M6PR ORF 29 Dec 95

E N L . V L D F . L S . E D M . L I . S I D R . Q R S S . P   Functional similarity
271       E N L E V L E F Q L S D E D M Q L I Y S I D R K Y R T S L P   A6PR protein aa
270       E N I N I F D F E L S K E D M E L I K T M E R N Q R S N T P   M6PR ORF 29 Dec 95

. K . W G L D V Y A .                                         Functional similarity
301       S K T W G L D V Y A                                           A6PR protein aa
300       A K A W G I D V Y A                                           M6PR ORF 29 Dec 95
```

Consensus 'Functional similarity': When all match the residue group of the
Consensus show the residue of the Consensus, otherwise show '.'. Residue
Groupings of Functional similarity are: a=(DE), b=(HKR), f=(AFILMPVW),
p=(CGNQSTY).

Decoration 'Decoration #1': Box residues that match M6PR ORF 29 Dec 95 exactly.

FIG. 4B

DNA ENCODING MANNOSE 6-PHOSPHATE REDUCTASE AND RECOMBINANTS PRODUCED THEREFROM

This application is a divisional of copending application Ser. No. 08/731,320 filed on Oct. 15, 1996, now U.S. Pat. No. 6,416,985.

GOVERNMENT RIGHTS

This invention was developed under U.S.D.A. Contract No. 93-37100-8907 and 94-01439. The U.S. Government has certain rights in this invention.

BACKGROUND OF THE INVENTION (1) Field of the Invention

The present invention relates to a DNA encoding mannose 6-phosphate reductase (M6PR) which is part of the pathway which forms mannitol in plants. The DNA encoding M6PR was isolated from celery. When the DNA is transformed into a plant the resulting transformed plant can be more tolerant to environmental stresses in the form of dehydration, salinity and drought.

(2) Description of Related Art

In many plants, sucrose and starch are the primary products of photosynthetic carbon assimilation. In other species, however, acrylic polyols (e.g., sorbitol, mannitol) can also be primary products and account for between 15 and 60% of the assimilated carbon, depending on the species (Loescher, W. H., Physiol. Plantarum 70:553–557 (1987); Fox, T. C., et al Plant Physiology 82:307–311 (1986); Flora and Madore Planta 189:484–490 (1993); Loescher, W. H. and Everard, J. D., Photoassimilate Distribution in Plants and Crops, 185–207 (1996)), the stage of leaf development, (Davis, J. M., et al., Plant Physiol, 86:129–133 (1988) and environmental factors (e.g., salinity (Everard, J. D., et al., Plant Physiol, 106:281–292 (1994)) and water stress; Escobar-Gutierrez, A., et al., Plant Physiol suppl 105: abstract 575 (1994)). The influence of developmental and environmental factors suggest that the partitioning of photoassimilates between sugar alcohols, sucrose and starch is under strict metabolic control. This is consistent with the complexity and diversity of the control mechanisms known to govern sucrose and starch synthesis in species that do not synthesize sugar alcohols (Quick, W. P. and Schaffer, A. A., Sucrose metabolism in sources and sinks. In: Photoassimilate distribution in plants and crops: source-sink relationships. Zamski, E., and Schaffer A., (eds), Marcel Dekker, Inc.: pp 115–156 (1996); and Preiss, J. and Sivak, M. N., Starch synthesis in sinks and sources. In: Photoassimilate distribution in plants and crops: source-sink relationships. Zamski, E., and Schaffer A., (eds), Marcel Dekker, Inc.: pp 63–96 (1996)). There is, however, almost no equivalent information on the mechanisms by which polyol metabolism is regulated or integrated with these other pathways in sugar alcohol synthesizing species. Such mechanisms are of more than just esoteric interest since: (a) an estimated 30% of global annual carbon assimilation results in polyol production (Bieleski, R. L., Sugar alcohols. In: F. A. Loewus and W. Tanner, eds., Plant Carbohydrates I. Intracellular Carbohydrates, Encyc. Plant Physiol. Vol. 13A, New Series, Springer-Verlag, NY, pp. 158–192 (1982)), (b) many polyol producing species are of considerable economic value, and (c) substantial correlative evidence shows that polyols accumulate in higher plants subjected to stresses mediated at the cellular level by changes in water activity, suggesting a role in stress tolerance (Bohnert, Hans J., et al., The Plant Cell, 7:1099–1111 (1995); Ahmad, I., et al., New Phytol 82:671–679 (1979); Hirai, M., Plant Cell Physiol. 24:925–931 (1983); Everard, J. D., et al., Plant Physiol 106:281–292 (1994); Stoop, J. M. H., et al., Plant Physiol. 106:503–511 (1994)).

In recent years major advances in the understanding of sugar alcohol metabolism in higher plants have been facilitated by the detection, characterization, and purification of several key enzymes (see Loescher and Everard, Photoassimilate Distribution in Plants and Crops, 185–207 (1996) for a review). The successful cloning of genes for NADP-dependent sorbitol 6-phosphate reductase (Kanayama, Y., et al., Plant Physiology 100:1607–1608 (1992)), mannose 1-oxidoreductase (Williamson, J. D., et al., Proc. Natl. Acad. Sci. 92:7148–7152 (1995)) and the introduction of heterologous genes, which confer sugar alcohol synthesis to plants that normally do not produce them (Tarczynski, M. C., et al., Science 259:508–510 (1993); Thomas, J. C., et al., Plant Cell and Environ 18:801–806 (1995); Tao, R., et al., Plant Cell Physiol 36:525–532 (1995)), now provide powerful tools with which to study sugar alcohol biochemistry and physiology. For example, Tarczynski, M. C., et al. (Science 259:508–510 (1993)), and Thomas, J. C., et al. (Plant Cell and Environ 18:801–806 (1995)) have recently shown that transgenic tobacco and Arabidopsis plants expressing the bacterial mannitol dehydrogenase (mtlD) gene not only produce low levels of mannitol, but also exhibit enhanced sodium chloride tolerance. In another study the inhibitory effects of 300 mM NaCl on the growth of celery suspension cultures were substantially reduced when mannitol, rather than sucrose, was included as the sole carbon source (Pharr, D. M., et al., Plant Physiology 180–194 (1995)). Such studies convincingly demonstrate that polyols confer some stress protection but give little insight into the underlying mechanisms. Mechanisms are beginning to be elucidated however, mannitol accumulation in salt stressed celery plants has been associated with a down regulation (at both the mRNA and protein levels) of mannitol dehydrogenase (MTD), a key catabolic enzyme (Williamson, J. D., et al., Proc. Natl. Acad. Sci., 92:7148–7152 (1995)), although, enhanced de novo synthesis is also undoubtedly involved in this acclimation response (Everard, J. D., Plant Physiol. 106:281–292 (1994); Loescher, W. H., et al., Plant Physiology, 170–178 (1995)). Other evidence showing a possible role for polyols in stress metabolism in higher plants includes the identification of an aldose reductase in Craterostigma leaves and barley embryos that accumulates when these tissues undergo desiccation (Bartels, D., et al., EMBO J 10:1037–1043 (1991)).

A pathway for mannitol synthesis in higher plants has been established in celery (Rumpho, M. E., et al., Plant Physiol. 73:869–873 (1983)) and appears to be present in other mannitol synthesizing species (Harloff, H. J., et al., J. Plant Physiol 141:513–520 (1993)). Biosynthesis involves three unique enzymatic steps consisting of an isomerization (F6P to mannose 6-P, mediated by mannose 6-P isomerase), a reduction (mannose 6-P to mannitol 1-P by mannose 6-P reductase (M6PR)) and a dephosphorylation (mannitol 1-P to mannitol, by mannitol 1-P phosphatase). Radiotracer studies and kinetic analyses indicate that M6PR plays a regulatory role in this pathway. This enzyme has been purified and partially characterized (Loescher, W. H., et al., Plant Physiol. 98:1396–1402 (1992)).

U.S. Pat. No. 5,268,288 to Pharr describes mannitol oxidoreductase protein. The enzyme converts mannitol to mannose in plants. It is thus different from the present invention which relates to mannitol production. The patent describes various recombinant techniques useful in the present invention. U.S. Pat. No. 5,492,820 to Sonnewald et al describes plasmids (vectors) for producing recombinant plants with altered sugar expression. The disclosure of such vectors is incorporated into the disclosure of the present application as well.

OBJECTS

It is therefore an object of the present invention to provide DNA encoding mannose 6-phosphate reductase (M6PR) which is useful in producing plasmids and transgenic plants with increased tolerance to environmental stresses, particularly salinity. These and other objects will become increasingly apparent by reference to the following description and the drawings.

BRIEF DESCRIPTION OF THE DRAWINGS

FIG. 2A is a graph showing M6PR activities in sonicated extracts of one nonspecific and three putative M6PR clones with and without IPTG induction. FIG. 2B is a photograph of an SDS gel of the extracts (100 $\mu$g/lane); the extreme right-hand lane contains 3 $\mu$g of authentic celery leaf M6PR. FIG. 2C is a photograph of a Western blot; an SDS gel containing 5 $\mu$g total protein per lane was blotted to PVDF membrane and probed with M6PR-specific antisera, as in Panel C the extreme left-hand lane contains authentic leaf enzyme.

FIGS. 3A and 3B are drawings showing the nucleic and translated amino acid sequence of celery cDNA clone D of SEQ ID NO:1 and SEQ ID NO:2, respectively. The open reading frame (M6PR ORF) coded for a peptide of 35.2 kD and had three domains which were identified, through computer data base searches, as being typical of the aldoketo reductase family. Also shown is the peptide resulting from tryptic digestion of authentic celery leaf M6PR and the Xho 1 restriction site within the coding region. Two other independent clones were sequenced on both strands and only differed from the displayed sequence in the lengths of their 3' and 5' non-coding regions.

FIGS. 4A and 4B are drawings showing an amino acid sequence comparison of M6PR of SEQ ID NO:2 and NADP-sorbitol-6-phosphate dehydrogenase from apple SEQ ID NO:4. Sequences were 64% identical (shown by enclosed areas) and showed 84% similarity, if the functional relatedness of the residues was considered. For the latter comparison the following groups were used: acidic (D,E), basic (H,K,R), hydrophobic (A,F,I,L,M,P,V,W) and polar (C,G,N,Q,S,T,Y); "." indicates lack of functional similarity.

DESCRIPTION OF PREFERRED EMBODIMENTS

Figure 1:
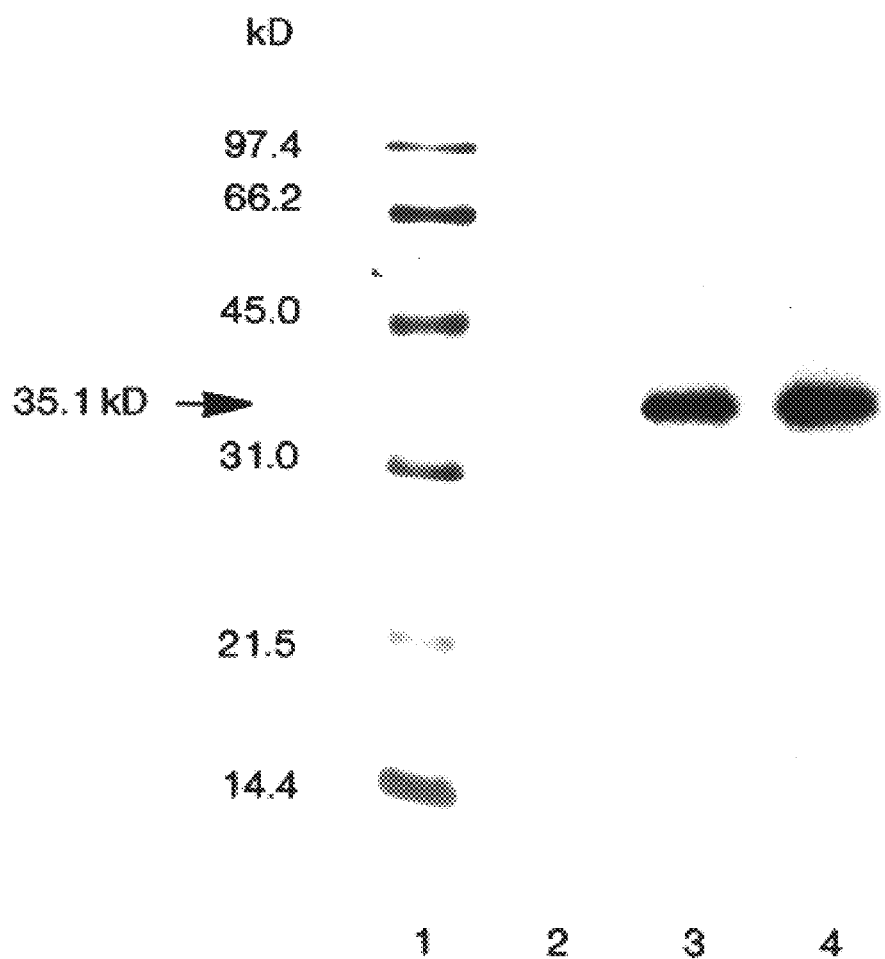
FIG. 1 is a photograph of an electrophoresis gel showing in vitro translation of poly(A)+RNA isolated from celery leaf tissue. Lanes 1 and 2 are Coomassie Brilliant blue R250 stained lanes from a 12.5% polyacrylamide gel showing Bio-Rad (Richmond, Calif.) molecular weight markers and purified celery leaf M6PR (0.1 $\mu$g), respectively. Lanes 3 and 4 show an autoradiograph of a subsample of the in vitro translation products represented from leaves 5 and 7 after immunoprecipitation with M6PR-specific antisera; all lanes were from the same gel.

The present invention relates to a DNA encoding mannose-6-phosphate reductase (M6PR) free of any other DNA as set forth in SEQ ID NO:1.

The present invention also relates to a DNA encoding mannose-6-phosphate reductase (M6PR) in a plasmid in an *Escherichia coli* as contained in a deposit identified as ATCC 98041.

The present invention also relates to a recombinant plasmid containing DNA encoding mannose-6-phosphate reductase as set forth in SEQ ID NO:1.

The present invention also relates to a recombinant plasmid containing DNA encoding mannose-6-phosphate reductase in a plasmid in *E. coli* as contained in a deposit identified as ATCC 98041.

The present invention also relates to a bacterium containing a recombinant plasmid containing DNA encoding mannose-6-phosphate as set forth in SEQ ID NO:1.

The present invention also relates to a bacterium containing a recombinant plasmid containing DNA encoding mannose 6-phosphate in the plasmid in an *E. coli* as contained in a deposit identified as ATCC 98041.

The present invention also relates to a method for detecting unknown DNA encoding mannose-6-phosphate reductase (M6PR) which comprises probing the unknown DNA with a probe DNA encoding a unique region of the M6PR as set forth in SEQ ID NO:1.

The present invention also relates to a method for detecting an unknown DNA encoding mannose-6-phosphate reductase (M6PR) which comprises probing the unknown DNA with a probe DNA encoding a unique region of the M6PR in a plasmid in *E. coli* as contained in a deposit identified as ATCC 98041.

The present invention also relates to a transgenic plant containing recombinant DNA encoding mannose-6-phosphate reductase (M6PR) based upon SEQ ID NO:1. The antisense of SEQ ID NO:1 is used.

The present invention also relates to a transgenic plant containing recombinant DNA encoding mannose-6-phosphate reductase (M6PR) in a plasmid in an *E. coli* contained in a deposit identified as ATCC 98041.

The present invention also relates to a method for detecting mannose 6-P reductase (M6PR) which comprises:
 (a) reacting an antibody selective for binding to the M6PR for screening an expression library suspected of encoding the M6PR; and
 (b) detecting the antibody binding to the M6PR.

The present invention also relates to a method for producing mannose 6-phosphate (M6PR) which comprises:
 (a) providing a bacterium containing a recombinant DNA encoding mannose-6-phosphate reductase (M6PR) free of any other DNA as set forth in SEQ ID NO:1 in a culture medium;

(b) expressing the M6PR in the culture medium; and (c) isolating the M6PR.

The present invention also relates to a method for producing mannose 6-phosphate reductase (M6PR) which comprises:

(a) providing a bacterium containing a recombinant plasmid containing DNA encoding mannose 6-phosphate reductase in the plasmid in an *E. coli* as contained in a deposit identified as ATCC 98041 in a culture medium;

(b) expressing the M6PR in the culture medium; and (c) isolating the M6PR.

The cloning of cDNAs encoding M6PR and the partial purification and characterization of active M6PR isolated from transformed *E. coli* is described.

The DNA of celery (*Apium graveolens*) encoding M6PR was deposited with the American Type Culture Collection on Apr. 30, 1996 in the BLUESCRIPT UNI-ZAP XR (Stratagene, LaJolla, Calif.) plasmid described and claimed in U.S. Pat. No. 5,128,256 contained in *Escherichia coli* SOLR and deposited as ATCC 98041. The plasmid contains a 1.3 kbp insert which is cleaved with Eco R1 and Kpn1 restriction enzymes. The culture is grown in the presence of 50 µg/ml ampicillin in LB media. No rights are granted to the DNA encoding M6PR except those accorded by the Budapest Treaty.

For M6PR, DNA encoding sequence is shown in SEQ ID NO:1. The encoded M6PR is shown in SEQ ID NO:2 and in FIGS. 3A and 3B. For aldose 6-phosphate reductase (S6PR), the DNA sequence is shown in SEQ ID NO:3 and the encoded S6PR is shown in SEQ ID NO:4. FIGS. 4A and 4B show the alignment of M6PR and S6PR as set forth in SEQ ID NO:2 and SEQ ID NO:4.

EXAMPLE 1

Isolation of M6PR Encoding DNA

Methods

RNA Isolation and Poly(A)+RNA Selection

Total RNA was extracted from approximately 10 g samples of the fifth and seventh leaves of mature celery (*Apium graveolens* c.v., Giant Pascal) plants, according to Gilmour, S. J., et al., Plant Physiol. 87:745–750 (1988)). Slight modifications includes: (a), addition of the polyphenol oxidase inhibitors cupferron (1 mM) and 2-mercaptobenzothiazole (1 µg/ml) to the extraction buffer immediately to prior use; (b), inclusion of three phenol:chloroform:isoamyl alcohol (25:24:1 v:v:v) partitioning steps on the aqueous phase, followed by three chloroform/isoamyl alcohol (49:1 v:v) partitionings to remove residual phenol; (c), a single LiCl precipitation followed by four ethanol precipitation steps. Total RNA yields (as determined by $OD_{260}$) averaged 500±180 µg/gFwt. The absence of contaminating DNA was confirmed on an agarose gel after RNAase treatment.

Poly(A)+RNA was isolated by oligo-dT-cellulose chromatography essentially as described by Sambrook et al (Molecular cloning. Cold Spring Harbor Laboratory Press, NY (1989)) but using a modified loading buffer (0.12 M NaCl, 0.01 M Tris-HCl pH 7.5, 0.001 M EDTA). Poly(A)+RNA was eluted from the column in the above buffer with the NaCl omitted.

In vitro Translation and Immunoprecipitation

1 µg of poly(A)+RNA from each leaf was translated in vitro using rabbit reticulocyte lysates (Promega Corp., Madison, Wis.) and [$^{35}$S] methionine, according to the suppliers directions. Translation products, after 1 h at 30° C., were separated by SDS-PAGE (Laemmli, U. K., Nature 227:401–407 (1970)) either, before (total) or after, immunoprecipitation (Hondred, D., et al., Plant Mol. Biol., 9:259–275 (1987)) with M6PR-specific antisera (Ried, J. L., et al., BioTechniques 12:660–666 (1992)).

cDNA Library Construciton

A unidirectional cDNA expression library was constructed in UniZap™ XR vector (Stratagene, LaJolla, Calif.) using a mixture of poly(A)+RNA from leaves 5 and 7 (2.5 µg of each). After packaging the phage library was amplified once before screening.

Library Screening

Two hundred thousand plaque forming units (pfu's) were screened for M6PR expression at a density of 40,000 pfu's per 140 mm Petri dish. Once phage plaques became visible (after approximately 3 h at 42° C.), nitrocellulose disks (previously soaked in 10 mM IPTG and then air-dried) were laid onto the surface of the plates and the cultures were incubated for a further 3.5 h at 37° C. The membranes were replaced with fresh IPTG soaked membranes and the cultures were incubated for a further 3 h. Both sets of membranes were screened using M6PR-specific antisera (Ried et al., BioTechniques 12:660–666 (1992)) at a dilution of 1:10,000 (see Everard et al., Plant Physiol 102:345–356 (1993), for methods used). Over 100 plaque giving positive signals in the initial screening were recovered from the plates and ten of these were subjected to two additional rounds of screening. Twelve other recombinant (as determined by α-complementation; Sambrook et al., Molecular cloning. Cold Spring Harbor Laboratory Press, NY (1989)) plaques that did not give a positive reaction with M6PR antisera were also selected as non-specific control clones.

After selection through three rounds of screening, clones (both putative-M6PR and nonspecific) were in vivo excised to yield phagemid (plasmid) clones in *E. coli* strain SOLR (Stratagene, LaJolla, Calif.). It should be pointed out that although 10 individual M6PR-putative clones were selected for further study it is not certain that these represented 10 individual mRNA's isolated from the original population in the leaf material used. This is because the original library was amplified once before screening (see above).

Sequencing of M6PR Clones

Three putative-M6PR clones were sequenced on both strands with an Applied Biosystems 373A sequencer using dye-primer and dye-terminator methodologies. Sequences were obtained using T3, T7 and 20-mer primers corresponding to internal sequences. Consensus sequence was derived by matching the two strands of each individual clone and by comparison of the three independent clones.

Sequence analysis was performed using SeqEd (Applied Biosystems Inc., Foster City, Calif.) and Lasergene (DNASTAR Inc., Madison, Wis.). Sequence comparisons with other databases was performed through the National Center for Biotechnology Information via the BLAST server. Peptide comparisons were made through ExPASY-Prosite and PRINTS.

Clone Confirmation

Internal Peptide Sequencing

M6PR was found to be unsuitable for amino acid sequencing in the native state, presumably because of an N-terminus block. M6PR purified as described by Loescher et al., Plant Physiol. 98:1396–1402 (1992) was further purified by running approximately 200 mg on a preparative 10% polyacrylamide gel under denaturing conditions. After staining with Coomassie Blue R250 (0.05%, wt:v in acetic acid:methanol:$H_2O$; 10:40:50, v:v:v) for 2 minutes and destaining (in stain solvent alone) the band of gel containing the M6PR was excised and electroeluted (Hunkerpillar et al., Methods in Enzymology 91:227–236 (1983)). The eluted protein was dried in vacuo and taken up in 80% ethanol (to remove residual SDS). The precipitated protein was pelleted by centrifugation, and the pellet dissolved in 100 mM ammonium bicarbonate (pH 8.2) prior to digestion with trypsin at 37° C. for 16 h. Trypsin was added in two equal doses (2%, by weight at each addition), with the second dose added after 8 h digestion.

Digestion products were separated by reverse phase chromatography on a 1×25 mm column (Applied Biosystems) eluted in a 90 minute linear gradient of TFA (0.1% v:v in $H_2O$) and acetonitrile (90:9.91.5:0.085; acetonitrile:$H_2O$:TFA v:v:v), at a flow rate of 830 nl/sec. Prominent peptides (as detected by $OD_{212\ nm}$) were collected, dried down in vacuo, and subjected to amino acid sequencing on an Applied Biosystems 477A sequencer.

Test for M6PR Activity in Putative Clones

Three putative M6PR and one non-positive clone (as determined by antibody screening) were tested for M6PR activity. Duplicate 10 ml cultures of each clone were grown in LB+ampicillin (amp; 50 mg/ml). Once an average $OD_{600}$ of 0.5 had been attained one culture of each pair was induced by the addition of isopropyl-β-D-thiogalactopyranoside (IPTG; final concentration 10 mM). Control (uninduced) cultures had an equal volume of sterile water added. Cultures were maintained at 30° C. for a further 3 h and were harvested at an average $OD_{600}$ of 1.29±0.02. Cells were pelleted by centrifugation (2000×g for 5 min) and washed twice by resuspending the pellets in 5 ml Tris (100 mM, pH 7.5) containing 250 mM PMSF, with a centrifugation step between each wash. After the final wash pelleted cells were maintained on ice. Just prior to disruption the cells were resuspended in 4 ml of extraction buffer (100 mM Tris-HCl pH 7.5, 250 mM PMSF, 10 mM DTT and 0.1% Triton X-100) and transferred to blood dilution vials (American Scientific Products, McGaw Park, Ill.). Cells were ruptured by suspending the vial containing the cells 0.5 cm above the cuphorn probe of a Heat Systems W-385 sonicator (Misonics Farmingdale, N.Y.) and subjecting them to 2 minutes sonication at full power. Coolant was circulated around the vial to maintain the temperature at approximately 4° C. After sonication, 1.5 ml aliquots of the homogenate were centrifuged at 13,000×g for 5 minutes at 4° C. Supernatants were assayed for M6PR activity (Loescher et al., Plant Physiol. 98:1396–1402 (1992)); with at least two different aliquot volumes from each extract to test for linearity. Supernatant aliquots (containing approximately 100 mg of total protein) were precipitated by adding a 7 times volume of acetone. After standing overnight at −21° C. the samples were prepared by SDSPAGE and Western blotting as described in Everard et al., Plant Physiol 102:345–356 (1993).

Large Scale Preparations and Purification

One liter LB/amp cultures were initiated by the addition of 50 ml of an overnight culture of clone D (initial $OD_{600}$, approx., 0.15). At an $OD_{600}$ of approximately 0.25 IPTG was added to a final concentration of 1 mM and the culture was incubated by 30° C. until $OD_{600}$ was between 0.8 and 1.0 (after approximately 6 hours; a preliminary experiment showing that M6PR specific activity began to level off when $OD_{600}$>1.0). Cells were harvested by centrifugation and, after washing as described above, were frozen at −80° C. Prior to extraction, cells were thawed slowly on ice and ruptured by either: 1. Sonication: cells were suspended in 20 ml extraction buffer (see previous section for composition) in a blood dilution vial and sonicated for 5 min at full power. The homogenate was centrifuged (20,000×g for 10 min), the supernatant collected, and the pellet resuspended in 10 ml extraction buffer and sonicated for a further 5 min, this cycle was repeated three times: or 2. Decompression/shearing: Cells suspended in 20 ml extraction buffer were ruptured by three passes through a French Press followed by centrifugation (20,000×g for 20 min).

Subsequent purification steps were essentially as described in Loescher et al., Plant Physiol. 98:1396–1402 (1992) except for Reactive Yellow 86 (RY86) chromatography. Here the active fraction from the gel filtration step was split in two, and each fraction run separately on the RY86 column as described in Loescher et al., Plant Physiol. 98:1396–1402 (1992). The active fractions were pooled and either diluted by the addition of 0.5 v of column buffer or desalted using centrifugal concentrating devices (30 kD cut-off membranes) and washed with 2 volumes of column buffer. This step was performed to dilute or remove NADPH. The sample was then loaded back onto the RY86 column and activity eluted in a linear gradient between 0 and 0.2 mM NADPH in column buffer. The purified M6PR was desalted and concentrated using centrifugal filtration and was either used immediately for kinetic characterization or stored at −21° C. after adding glycerol (1:1, v:v).

Protein Determinations

Protein content was determined by the method of Bradford, M. M., Anal Biochem 136:248–254 (1976) using Bovine Serum Albumen (BSA) as a standard.

Results

Characteristics of M6PR-specific Immunoprecipitation Products

FIG. 1 shows that immunoprecipitation (with M6PR-specific antisera) of the in vitro translation products synthesized from poly(A)+RNA isolated from leaves 5 and 7 yielded a single dominant peptide (molecular mass, 35.1 kD) from each leaf. The molecular mass of authentic celery M6PR run on the same gel (but not immunoprecipitated) was 35.1 kD; immunoprecipitation prior to SDSPAGE had no effect on the relative mobility of M6PR (data not shown). Five and seven percent of the total TCA precipitatable radioactivity was recovered in the immunoprecipitation products from leaves 5 and 7, respectively.

Characteristics of the cDNA Library

The primary library consisted of >1.5×10$^6$ plaque forming units (pfu's) of which 0.33% were non-recombinant, as estimated by α-complementation. Phagemids from 12 randomly selected recombinant clones were in vivo excised and used to transform E. coli (strain SOLR). The average insert size (after digestion with Eco R1 and Xho 1) was 1.7 kb, with a size range between 1.0–2.3 kb.

Library Screening

Of the 200,000 pfu's screened an estimated 0.15±0.04% gave a positive signal with M6PR-specific antisera and were thus identified as putative M6PR clones. Ten of these were subjected to two more rounds of screening and three of these were characterized and their authenticity as M6PR clones was confirmed as described below.

Expression of M6PR Enzyme Activity

Figure 2A:
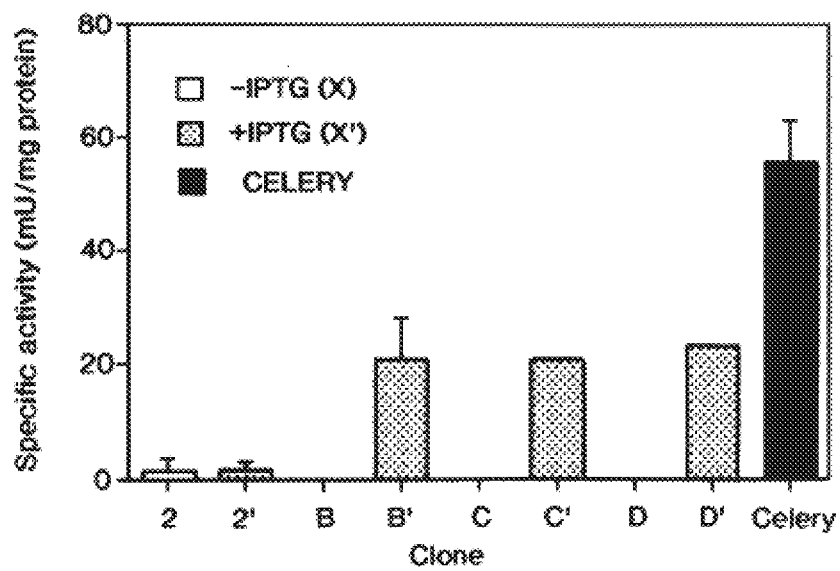
FIGS. 2A, 2B and 2C show verification of M6PR specific clones.
Figure 2B:
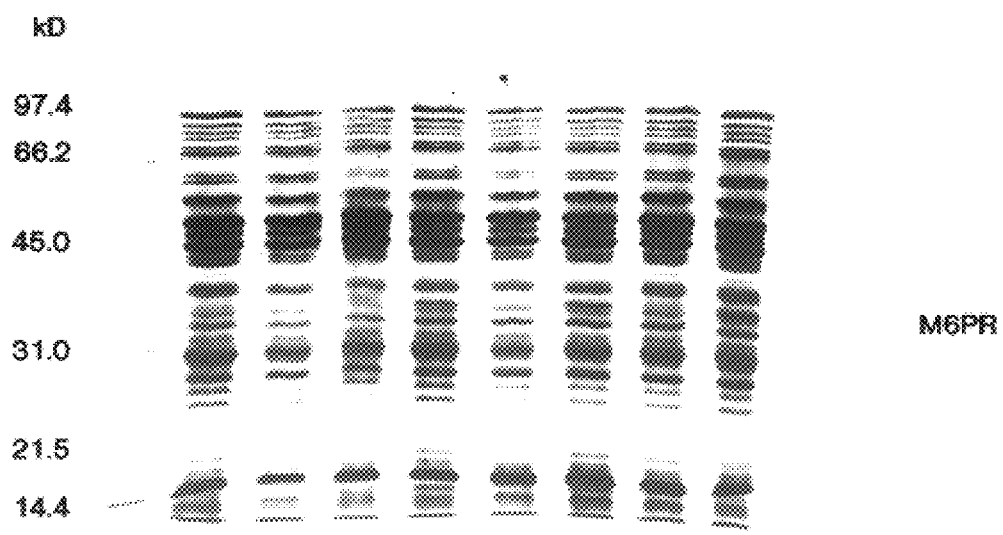

FIG. 2A shows the activity of M6PR, in one non-specific (2) and the three putative M6PR clones (B, C and D), with and without induction with IPTG. Under IPTG induction, the putative M6PR-specific clone expressed M6PR activity, whereas little or no activity was observed in the non-specific clone (2), with or without IPTG induction, or in the uninduced cultures of the putative specific clones. The presence and absence of a peptide with identical molecular mass to authentic celery M6PR (FIG. 2B), which also reacted with M6PR-specific antisera (FIG. 2C), correlated well with the measured enzyme activities. Trace amounts of M6PR peptide were detected in uninduced cultures of the specific clones (FIG. 2C) but the levels were below that detectable in the enzyme assay (FIG. 2A). This experiment was repeated twice with identical results.

Sequencing M6PR Clones

Figure 3A:
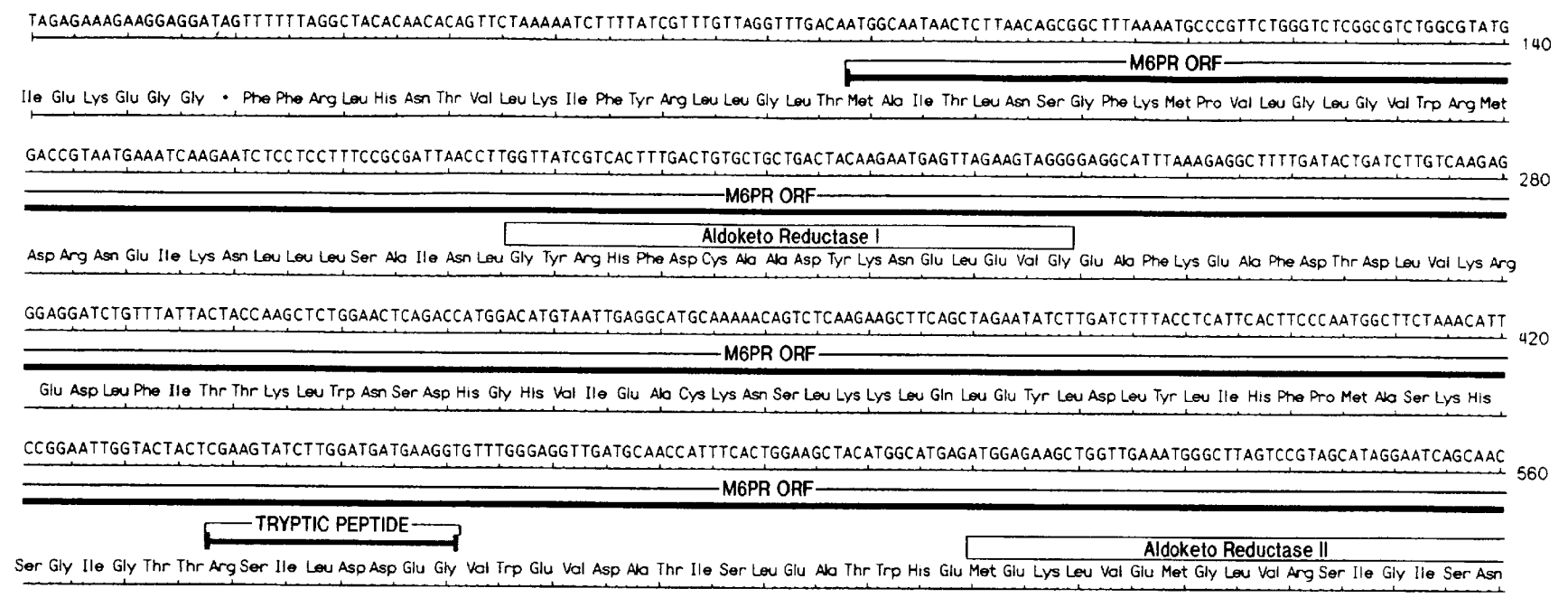

EcoR1-Kpn1 restriction digestion of the three putative M6PR clones yielded inserts of approximately 1.3 kb. The sequence of one of these inserts is shown in FIGS. 3A and 3B. The sequence of the two other putative clones was also determined (data not show). Each of the sequenced inserts coded for a 927 bp open reading frame; the clones differed from each other in the length of the 5' non-coding region and the poly-A tail, suggesting that they represent independent cloning events rather than duplications arising during library amplification. Translation of the open reading frame yielded a polypeptide with a molecular mass of 35.2 kD (FIGS. 3A and 3B). This value was consistent with the previously determined value for authentic celery M6PR (determined by SDS-PAGE) of 34.5 kD (Loescher et al., Plant Physiol. 98:1396–2401 (1992)) and with MALDITOFMS determined values for the recombinant and authentic M6PR protein (see below, Table 3). The predicted translation product was also consistent with an internal peptide sequence obtained after tryptic digestion of purified celery M6PR. The predicted translation product was identical to the internal amino acid sequence R, S, I, L, D, D, E, G (Arg Ser Ile Leu Asp Asp Glu Gly) (FIGS. 3A and 3B). A search of the non-redundant data base at NCBI gave only one entry showing homology (*Mycoplasma pneumoniae* M129B18 cytadherence-accessory) indicating the rarity of this specific sequence.

Sequence Comparisons

Sequence similarities resulting from a search of the NCBI non-redundant data base resulted in 61 entries showing greater than 55% sequence homology with either the whole length of defined regions of the M6PR ORF. This information and an analysis of the amino acid sequence of M6PR through two motif analysis programs (see Materials and Methods) showed M6PR to be a member of the aldoketo reductase family. A detailed description of the features and members of this group can be gained from Bohren et al., J. Biol. Chem. 264:9547–9551 (1989). In brief, the group is typified by the three conserved domains marked in FIGS. 3A and 3B.

Five sequences of plant origin were obtained from the nucleotide sequence comparison (listed in Table 1).

TABLE 1

Sequence similarity between M6PR and entries accessible through the National Institute of Biotechnological Information (NCBI) data base.

| Accession # | Clone Identity | Comparable sequence | % Identity |
|---|---|---|---|
| D11080 | Apple S6PDH NADP-dependent mRNA | Full mRNA | 66 |
| Z48383 | *Arabidopsis thaliana* 315 bp EST | bases 14–325 of M6PR ORF | 70 |
| D41273 | *Oryza sativa* (Rice) 462 bp EST | bases 3–291 of M6PR ORF | 67 |
| D48175 | *Oryza sativa* 430 bp EST | bases 118–331 of M6PR ORF | 73 |
| X57526 | *Hordeum vulgare* (Barley) aldose reductase | Bases 413–635 | 53 |

A direct sequence comparison with NADP-dependent sorbitol-6-phosphate dehydrogenase, which showed the greatest degree of homology over the entire M6PR sequence, is given in FIGS. 4A and 4B.

Purification and Characterization of Recombinant M6PR

Table 2 shows the results of a typical purification of M6PR from clone D.

TABLE 2

Summary of a typical purification of recombinant M6PR from a 1 liter, IPTG induced, culture of clone D.

| STEP | vol (ml) | protein (mg) | Total Activity (mU) | Specific Activity (mU/mg prot) | Yield (%) | Purification (X) |
|---|---|---|---|---|---|---|
| Crude | 22.5 | 178 | 13433 | 75 | 100 | 1 |
| 30–60% acetone | 10 | 79 | 14155 | 179 | 105 | 2.4 |
| S200 gel filt. | 67 | 77 | 12663 | 164 | 94 | 2.18 |
| RY 86, 2 passes | 4 | 0.5 | 2216 | 4432 | 16 | 59 |

1 mU = 1 nmol NADPH oxidized per minute. RY 86 = Reactive Yellow 86 affinity chromatography. On the first pass M6PR was eluted with 0.1 mM NADPH, on the second pass M6PR was eluted with a linear gradient of 0 to 0.2 mM NADPH. At the end of the purification the enzyme was concentrated and NADPH was removed by ultrafiltration. Buffers used during the purification and the assay conditions were as described in Loescher et al., 1992.

Figures 5A, 5B:
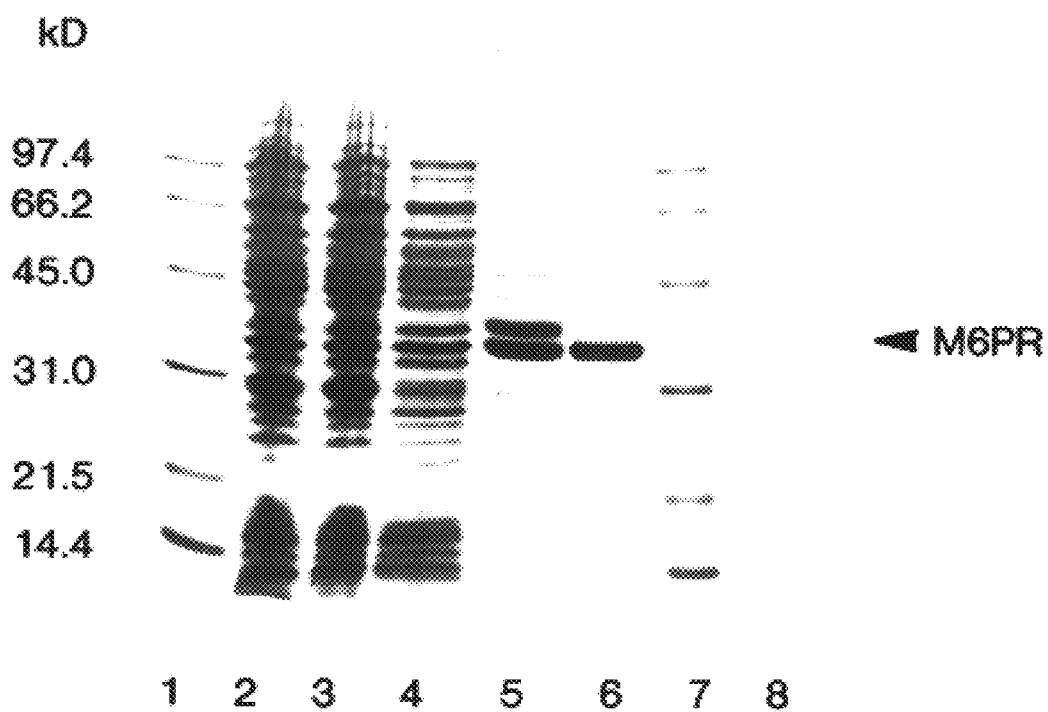
FIG. 5A is a photograph of SDSPAGE gel (12.5% acrylamide) of samples collected after the various purification steps (See Table 2). Lanes: 1 and 7, Bio-Rad molecular mass markers; 2, 27,500 g supernatant of disrupted cells (80 $\mu$g protein); 3, 30 to 60% acetone fraction (120 $\mu$g); 4, post gel-filtration chromatography on Sephacryl S-200 (30 $\mu$g); 5, post affinity chromatography on Reactive Yellow 86 eluted with 0.1 mM NADPH (15 $\mu$g); 6, product of a second pass over the RY86 column eluted with a linear gradient (0 to 0.2 mM) of NADPH (2 $\mu$g). 8, authentic celery leaf M6PR (0.5 $\mu$g).
FIG. 5B is a photograph of a Western blot of proteins from selected purification steps (see above), probed with M6PR-specific antisera. Lanes: 1, 6 and 7 authentic celery leaf M6PR; 2, crude supernatant; 3, post S200 gel filtration; 4 and 5, after 1 and 2 passes over the RY86 affinity column, respectively.

With RY86 purification and desalting, a 50 to 60 fold purification was achieved. The average specific activity of the purified recombinant enzyme, 3926±833 mU/mg protein (average of three preparations; final two preparations 4441±13 mU/mg), was comparable to that of purified celery M6PR (3756 mU/mg protein, Loescher et al., Plant Physiol. 98:1396–1402 (1992)). FIG. 5A shows an SDS-PAGE of the various purification steps. After the second pass over the RY86 column the dominant peptide, which had a molecular mass identical to authentic celery M6PR (FIG. 5A) and cross reacted with M6PR-specific antisera (FIG. 5B) represented 88±4% of the protein present (estimated by scanning densitometry; mean of 2 independent preparations).

Characterization of Recombinant M6PR

Table 3 shows some characteristics of M6PR purified from the two sources.

TABLE 3

A comparison of the characteristics of purified leaf and recombinant M6PR.

| | Authentic leaf M6PR | Recombinant M6PR |
|---|---|---|
| SDSPAGE determined Molecular mass. (kD) | 34.8 ± 0.4 (2;3) | 34.3 ± 0.4 (2;3) |
| MALDITOFMS determined Molecular mass. (kD) | 35.21 (1;1) | 35.3 ± 0.01 (1;3) |
| $V_{max}$; mannose 6-P ($\mu$mol mg prot$^{-1}$ min$^{-1}$) | 6.8 ± 1.3 (2;2) | 8.0 ± 1.9 (4;6) |
| $k_m$; mannose 6-P (mM) | 13.6 ± 2.7 (2;2) | 10.1 ± 1.4 (4;6) |
| $V_{max}$; NADPH ($\mu$mol mg prot$^{-1}$ min$^{-1}$) | 3.7 ± 0.7 (2;2) | 6.0 ± 2.3 (2;2) |

TABLE 3-continued

A comparison of the characteristics of purified leaf and recombinant M6PR.

|  | Authentic leaf M6PR | Recombinant M6PR |
|---|---|---|
| $k_m$; NADPH ($\mu$M) | 2.1 ± 1.1 (2;2) | 6.2 ± 2.4 (2;3) |

SDSPAGE determined molecular masses of purified authentic and recombinant M6PR were determined by running them in adjacent wells on 12.5% acrylamide gels. MALDITOFMS = Matrix Assisted Laser Desorption Ionization Time Of Flight Mass Spectrometry; the matrix was sinapinic acid. The values within parentheses represent the number of individual enzyme preparations and the number of independent determinations used to calculate the mean of each parameter, respectively. Kinetic parameters were determined at 30° C. in 33 mM Tris-HCl buffer (pH 7.5) containing 3 mM DTT (see Loescher et al. (1992) for other details concerning the assays). Mannose 6-phosphate (M6P) kinetics were determined at 12 concentrations of M6P ranging from 1–50 mM under saturating NADPH concentrations (200 $\mu$M). NADPH kinetics were determined at 9 NADPH concentrations ranging from 1–50 $\mu$M. Mannose 6-phosphate concentrations in these assays were 12 mM. Best line fits on double reciprocal plots were calculated by linear regression. At least 4 data points were used for the regression analyses (in most cases more than 8); $r^2$ values were >0.99 except for one recombinant NADPH determination The molecular masses of the authentic and the recombinant proteins determined by either SDS-PAGE or MALDITOF were almost identical and both were consistent with the value of 35.2 kD determined by translation of the coding region (see above). The $V_{max}$ and $k_m$ values determined for mannose 6-phosphate were the same for both enzymes (Table 3) and those determined for NADPH were not significantly different (by t-test).

In this Example 1 shows the successful cloning of a full length transcript coding for mannose 6-phosphate reductase from celery. This represents the first report of the cloning of the purification of competent recombinant enzyme from transformed E. coli. The purified recombinant protein had physical and kinetic properties indistinguishable from the purified plant enzyme.

Figure 2C:
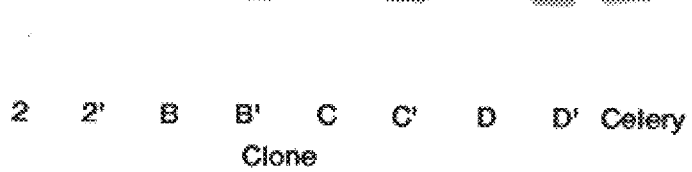

The authenticity of the clones was confirmed by the following criteria. 1). Only putative clones displayed M6PR activity when induced with IPTG. The activity correlated with the presence of a peptide, of identical molecular mass to authentic celery leaf M6PR (Table 3). This peptide cross reacted with M6PR-specific antisera (FIG. 2C). No activity or immuno reactive peptide was observed in non-specific clones. 2). A tryptic digestion product from authentic celery M6PR had 100% homology to a peptide present within the open reading frame of the putative clone (FIGS. 3A and 3B). 3). Database comparisons showed that the clones had a high degree of homology to the aldo-keto reductase family. The greatest degree of homology (spanning the whole ORF with 67% sequence and 64% amino acid identity; 84% similarity when amino acids with the same functional properties were considered (FIGS. 4A and 4B)) was with NADP-dependent D-sorbitol 6-phosphate dehydrogenase (Kanayama et al., Plant Physiology 10:1607–1608 (1992)), a key enzyme in sorbitol biosynthesis in woody Rosaceae species. The sequence and amino acid similarity was very low (<22%) on an amino acid and sequence comparison basis) between M6PR and mannitol dehydrogenase (MTD; Williamson et al., Proc Natl. Acad. Sci. 92:7148–7152 (1995)), the only other mannitol metabolizing enzyme cloned to date from higher plants. However, four other similar plant sequences were obtained from the databases. Three of these were for partial sequences from arabidopsis and rice which showed strong homology with the 5' end of M6PR (Table 1). Although there are not known to be any reports of sugar alcohols in arabidopsis and rice, the recent discovery of a homologue of mannitol dehydrogenase in arabidopsis (Williamson et al., Proc. Natl. Acad. Sci. 92:7148–7152 (1995)) may indirectly confirm Bieleski's admonition that the presence of sugar alcohols should not be discounted until proven absent (Bieleski, R. L., Sugar Alcohols. In: F. A. Loewus and W. Tanner, eds., Plant carbohydrates I. Intracellular Carbohydrates, Encyc. Plant Physiol., Vol. 13A, New Series. Springer-Verlag, NY, pp. 158–192 (1982)). The fifth plant enzyme sequence with similarity to M6PR was an aldose reductase from barley (see below). As mentioned, there is almost no information as to how sugar alcohol metabolism is regulated and integrated with the other products of primary production (sucrose, starch and nitrogen metabolism) in higher plants. In contrast, there is a relatively large body of work on the kinetics and regulation of animal aldose reductase, driven by their putative role in the pathology of diabetes mellitus (Borhani, D. W., et al., J. Biol. Chem. 267:24841–24847 (1992)). The sequence homologies suggest that insights into regulatory sites and mechanisms in the plant enzymes may be gained from the animal literature. For example, several sites are highly conserved between the animal and plant enzymes (marked as motifs 1, 2 and 3 in FIG. 3B) including the peptide IPKS (within motif 3, towards the 3' end of the coding region). The lysine (K) within this motif has been shown, by chemical modification studies in animals, to be the likely NADPH binding site (Morijana et al., FASEB J 46:1330 (abstract) (1987); Bohren et al., J. Biol. Chem. 264:9547–9551 (1989)). This motif is completely conserved in terms of amino acids and position in M6PR (IPKS, amino acids 260–264), NADP-dependent D-sorbitol 6-phosphate dehydrogenase (IPKS, amino acids 260–264) and in aldose reductase (IPKS, amino acids 257–260) cloned from desiccated barley embryo's (Bartels et al., EMBO J 10:1037–1043 (1991)). This latter aldose reductase has been associated with tissues subjected to desiccation and is inducible with ABA which is of interest given the role that mannitol synthesis and M6PR play in salinity stressed celery (Everard et al., Plant Physiol. 106:281–292 (1994); Loescher et al., Plant Physiology 170–178 (1995)). Another similarity between the animal aldose reductases and M6PR is the apparent lack of post-translational modification. In vitro translation of celery poly(A)+RNA resulted in a peptide immunoprecipitation product of identical molecular mass to authentic leaf M6PR (FIG. 1B) indicating that post-translational modification is unlikely to occur in vivo, a conclusion also drawn for bovine lens aldose reductase (the model for study of this class of enzymes prior to the availability of recombinant enzymes, Schade et al., J.B.C. 265(7):3628–3635 (1990). Finally, aldose reductases in animals are sensitive to oxidation (Petrash et al., JBC 267(34):24833–24840 (1992)), as is the M6PR (Loescher et al., Plant Physiol. 98:1396–1402 (1992)), and the current thinking is that redox activation/inactivation may play an important role in the in vivo regulation of M6PR. The importance of redox activation of extraplastidic plant enzymes has grown in recent years and an increasing number of cytosolic (Anderson et al., Planta 196:118–124 (1995)) and mitochondrial enzymes are being reported to be regulated in part by this mechanism. The recombinant enzyme has a specific activity similar to the plant enzyme which suggests that if redox activation is a factor then the E. coli thioredoxin system is competent. Such information should lead to approaches to look for regulatory mechanisms in the plant enzymes, studies that will be simpler with the recombinant enzyme which appears fully competent and kinetically indistinguishable from the authentic enzyme. Ultimately, mechanisms may be explored at the enzyme level using site directed mutagenesis and at the whole plant level by studies into message level regulation, such as that recently reported for NADP-dependent D-sorbitol 6-phosphate dehydrogenase (Kanayama et al., Plant Physiology 100:1607–1608 (1995)), and by pathway suppression using antisense and cosuppression techniques. Such studies should give insight into the roles of polyols in primary carbon metabolism and hence plant productivity as well as in stress tolerance.

DNA is incorporated into plants in a manner known to those skilled in the art as represented by U.S. Pat. No. 5,492,820 to Sonnewald et al. Various well known vectors are used.

EXAMPLE 2

A large number of techniques are available for inserting M6PR DNA into a plant host cell. Those techniques often include transformation with T-DNA using *Agrobacterium tumefaciens* or *A. rhizogenes* containing the Ti or Ri plasmids (respectively) as transformation agents. Some of the other methods used include fusion, biolistic or conventional injection, or electroporation. If Agrobacterium related methods are used, the DNA is cloned into a special plasmid, either an intermediate vector or into a binary vector. Intermediate vectors are integrated into the Ti or Ri plasmid by homologous recombination resulting from sequences that are homologous to sequences in the T-DNA. The Ti or Ri plasmid also comprises the vir region necessary for transfer of the T-DNA. The intermediate vector are transferred into Agrobacterium by means of a helper plasmid (via conjugation). Binary vectors replicate themselves both in *E. coli* and Agrobacterium. These vectors include a selection marker gene and a linker or polylinker that are framed by the right and left T-DNA border regions. These are transformed directly into Agrobacterium and the Agrobacterium is then used as a host cell for the plasmid carrying the vir region. The vir region is also necessary for the transfer of the T-DNA into the plant cell. Additional T-DNA may be contained. The transformed bacteria are used for transformation of plant cells. Plant explants (e.g., sections of leaves, stems and roots, segments of petioles, flowers, and flower parts) are cultivated with *Agrobacterium tumefaciens* or *A. rhizogenes* for the transfer of the DNA into the plant cell. Whole plants are then regenerated (from the infected plant material, or from protoplasts or suspension-cultivated cells) in a suitable medium which can contain antibiotics or biocides (e.g., kanamycin, bleomycin, hygromycin, chloramphenicol, among others) for selection of transformed plant cells. Unlike Agrobacterium-mediated insertion of M6PR DNA, no special demands are necessary for construction for plasmids used for particle bombardment, fusion, injection, or electroporation. It is possible to use ordinary plasmids, e.g., pUC derivatives, although selection markers are usually included. However obtained, whole plants are then tested for the presence of the inserted DNA. The transformed cells grow normally in the plant and eventually give rise to reproductive organs, i.e., flowers, that can be used in an ordinary breeding program. The resulting hybrids have the appropriate phenotypic properties.

Expression of the M6PR DNA requires a promoter associated with the cloned gene. Among the many examples available are viral promoters such as the cauliflower mosaic virus 35 S promoter, heat shock protein promoters such as the HSP 70 promoter, light induced promoters such as the ST-Ls1 or the rubisco small subunit (SSU) promoters, stress response proteins such as the PR protein promoter, the *Agrobacterium tumefaciens* nos promoter, and various organ, root, tuber (e.g., the class I patatin), and leaf specific promoters. A termination signal is also used in these constructs, e.g., the 3'-end of the poly-A side of the octopine synthase gene.

It is intended that the foregoing description be only illustrative of the present invention and that the present invention be limited only by the hereinafter appended claims.

We claim:

1. A method for detecting unknown DNA encoding mannose-6-phosphate reductase (M6PR) which comprises probing the unknown DNA with a probe DNA comprising a sequence or a portion of the sequence as set forth in SEQ ID NO:1.

2. A method for detecting unknown DNA encoding mannose-6-phosphate reductase (M6PR) which comprises probing the unknown DNA with a DNA probe comprising DNA encoding M6PR or a portion of the M6PR, the DNA probe including a region which is noncoding, in a plasmid in *E. Coli* as contained in a deposit identified as ATCC 98041.

3. A method for detecting whether DNA from a plant encodes mannose-6-phosphate reductase (M6PR) comprising:

(a) isolating the DNA from the plant; and (b) probing the DNA with a probe DNA encoding the M6PR or a portion of the M6PR DNA probe which has a sequence as set forth in SEQ ID NO:1, including a region in the DNA probe which is noncoding, wherein the probe hybridizes to the DNA which encodes the M6PR.

4. The method of claim 3 wherein the probe is the M6PR or the portion thereof in a plasmid in *Escherichia Coli* as contained in a deposit identified as ATCC 98041.

5. The method of claim 3 wherein the DNA is a cDNA of RNA from the plant.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1207
      (B) TYPE: Nucleic Acid
      (C) STRANDEDNESS:  Single
      (D) TOPOLOGY: Linear (ii) MOLECULE TYPE:
      (A) DESCRIPTION:  Synthetic DNA (iii) HYPOTHETICAL:  No (iv) ANTI-SENSE:  No (vi) ORIGINAL SOURCE:
      (A) ORGANISM: Celery (vii) IMMEDIATE SOURCE:
      (A) LIBRARY:

(xi) SEQUENCE DESCRIPTION: SEQ ID NO: 1:

```
TAGAGAAAGA AGGAGGATAG TTTTTTAGGC TACACAACAC         40

AGTTCTAAAA ATCTTTTATC GTTTGTTAGG TTTGACAATG         80

GCAATAACTC TTAACAGCGG CTTTAAAATG CCCGTTCTGG        120

GTCTCGGCGT CTGGCGTATG GACCGTAATG AAATCAAGAA        160

TCTCCTCCTT TCCGCGATTA ACCTTGGTTA TCGTCACTTT        200

GACTGTGCTG CTGACTACAA GAATGAGTTA GAAGTAGGGG        240

AGGCATTTAA AGAGGCTTTT GATACTGATC TTGTCAAGAG        280

GGAGGATCTG TTTATTACTA CCAAGCTCTG GAACTCAGAC        320

CATGGACATG TAATTGAGGC ATGCAAAAAC AGTCTCAAGA        360

AGCTTCAGCT AGAATATCTT GATCTTTACC TCATTCACTT        400

CCCAATGGCT TCTAAACATT CCGGAATTGG TACTACTCGA        440

AGTATCTTGG ATGATGAAGG TGTTTGGGAG GTTGATGCAA        480

CCATTTCACT GGAAGCTACA TGGCATGAGA TGGAGAAGCT        520

GGTTGAAATG GGCTTAGTCC GTAGCATAGG AATCAGCAAC        560

TATGATGTTT ACTTGACCAG AGATATCTTG TCATATTCCA        600

AGATCAAGCC TGCTGTAAAT CAGATCGAGA CGCACCCTTA        640

CTTCCAAAGA GATTCTCTGA TCAAATTCTG TCAGAAGTAT        680

GGCATTGCTA TCACAGCACA CACACCACTA GGCGGCGCAT        720

TGGCTAATAC TGAGCGATTT GGATCAGTTT CGTGCTTAGA        760

TGATCCAGTT CTTAAGAAAT TATCTGACAA ACACAACAAG        800

TCACCAGCTC AGATTGTTCT CCGTTGGGGT GTGCAGCGCA        840

ACACAATTGT AATTCCCAAG TCATCGAAAA CTAAAAGACT        880

CGAGGAAAAC ATCAACATTT TTGACTTTGA GTTGAGCAAG        920

GAAGATATGG AGCTCATCAA AACAATGGAG CGCAACCAAA        960

GGAGTAACAC ACCTGCTAAA GCTTGGGGAA TAGATGTTTA       1000

TGCTTGATGG CATAACACAT TCTTCACTGT ATTTTTATCA       1040

TTGTTATTCC ACAATTCAGA GTGGTTGTCA TTTTTACTTG       1080

CTATTGTGTG TGGAGGGGAA TGTGTGTTGA GTTGTTGTAG       1120

TAATTGTACA AGGCATAAAG CCTTTAAATA ACCCATCATA       1160

TGTAAATGGG AAATGCCATG ATTTGGTCAA AAAAAAAAA        1200

AAAAAAA                                           1207
```

(2) INFORMATION FOR SEQ ID NO:2:

(i) SEQUENCE CHARACTERISTICS:
        (A) LENGTH: 309
        (B) TYPE: Amino Acid
        (C) STRANDEDNESS: Single
        (D) TOPOLOGY: Linear (ii) MOLECULE TYPE:
        (A) DESCRIPTION:

(iii) HYPOTHETICAL: No (iv) ANTI-SENSE: No (vi) ORIGINAL SOURCE:
            (A) ORGANISM: celery (vii) IMMEDIATE SOURCE:
            (A) LIBRARY:

(xi) SEQUENCE DESCRIPTION: SEQ ID NO: 2:

Met Ala Ile Thr Leu Asn Ser Gly Phe Lys Met Pro Val Leu Gly
                 5                  10                  15

Leu Gly Val Trp Arg Met Asp Arg Asn Glu Ile Lys Asn Leu Leu
                20                  25                  30

Leu Ser Ala Ile Asn Leu Gly Tyr Arg His Phe Asp Cys Ala Ala
                35                  40                  45

Asp Tyr Lys Asn Glu Leu Glu Val Gly Glu Ala Phe Lys Glu Ala
                50                  55                  60

Phe Asp Thr Asp Leu Val Lys Arg Glu Asp Leu Phe Ile Thr Thr
                65                  70                  75

Lys Leu Trp Asn Ser Asp His Gly His Val Ile Glu Ala Cys Lys
                80                  85                  90

Asn Ser Leu Lys Lys Leu Gln Leu Glu Tyr Leu Asp Leu Tyr Leu
                95                 100                 105

Ile His Phe Pro Met Ala Ser Lys His Ser Gly Ile Gly Thr Thr
               110                 115                 120

Arg Ser Ile Leu Asp Asp Glu Gly Val Trp Glu Val Asp Ala Thr
               125                 130                 135

Ile Ser Leu Glu Ala Thr Trp His Glu Met Glu Lys Leu Val Glu
               140                 145                 150

Met Gly Leu Val Arg Ser Ile Gly Ile Ser Asn Tyr Asp Val Tyr
               155                 160                 165

Leu Thr Arg Asp Ile Leu Ser Tyr Ser Lys Ile Lys Pro Ala Val
               170                 175                 180

Asn Gln Ile Glu Thr His Pro Tyr Phe Gln Arg Asp Ser Leu Ile
               185                 190                 195

Lys Phe Cys Gln Lys Tyr Gly Ile Ala Ile Thr Ala His Thr Pro
               200                 205                 210

Leu Gly Gly Ala Leu Ala Asn Thr Glu Arg Phe Gly Ser Val Ser
               215                 220                 225

Cys Leu Asp Asp Pro Val Leu Lys Lys Leu Ser Asp Lys His Asn
               230                 235                 240

Lys Ser Pro Ala Gln Ile Val Leu Arg Trp Gly Val Gln Arg Asn
               245                 250                 255

Thr Ile Val Ile Pro Lys Ser Ser Lys Thr Lys Arg Leu Glu Glu
               260                 265                 270

Asn Ile Asn Ile Phe Asp Phe Glu Leu Ser Lys Glu Asp Met Glu
               275                 280                 285

Leu Ile Lys Thr Met Glu Arg Asn Gln Arg Ser Asn Thr Pro Ala
               290                 295                 300

Lys Ala Trp Gly Ile Asp Val Tyr Ala
               305

(2) INFORMATION FOR SEQ ID NO:3:

(i) SEQUENCE CHARACTERISTICS:
         (A) LENGTH: 1259
         (B) TYPE: Nucleic Acid
         (C) STRANDEDNESS: Single
         (D) TOPOLOGY: Linear (ii) MOLECULE TYPE:
           (A) DESCRIPTION: Synthetic DNA (iii) HYPOTHETICAL: No (iv) ANTI-SENSE: No (vi) ORIGINAL SOURCE:
           (A) ORGANISM: apple (vii) IMMEDIATE SOURCE:
           (A) LIBRARY: N/A (xi) SEQUENCE DESCRIPTION: SEQ ID NO: 3:

```
CCGCTCTAGA ACTAGTGGAC GAGAGAAAAA CAGAAACAGG                    40

CTGCAGCAGT CGCTGAGAGA GTTTGGAGAG TGAGAAAACA                    80

TGTCCACCGT CACCCTGAGC AGTGGCTACG AGATGCCGGT                   120

CATCGGTCTC GGCCTTTGGC GTCTGGAGAA GGACGAGCTT                   160

AAAGAAGTCA TCTTAAATGC TATTAAGATT GGCTATCGCC                   200

ATTTTGACTG TGCTGCTCAT TACAAGAGTG AAGCAGACGT                   240

TGGAGAAGCA CTTGCAGAAG CATTTAAGAC TGGACTTGTT                   280

AAGAGGGAAG AACTTTTCAT TACCACCAAG ATTTGGAATT                   320

CAGACCATGG GCATGTGGTG GAGGCCTGTA AGAACAGCCT                   360

CGAGAAGCTT CAGATAGATT ATCTGGATCT CTACCTGGTT                   400

CACTACCCAA TGCCCACAAA GCACAATGCA ATTGGTAAAA                   440

CTGCCAGTCT TTTGGGCGAG GATAAGGTGT TGGACATCGA                   480

TGTAACAATT TCCCTTCAAC AAACCTGGGA GGGCATGGAA                   520

AAGACCGTCT CTTTGGGCTT AGTTCGCAGC ATTGGTCTCA                   560

GCAACTATGA GCTCTTTCTA ACTAGAGATT GCTTGGCTTA                   600

CTCCAAAATA AAGCCTGCTG TGAGCCAATT TGAAACCCAC                   640

CCCTATTTCC AGCGCGACTC TCTCGTCAAA TTCTGTATGA                   680

AACACGGCGT TCTTCCCACA GCTCACACCC CTCTCGGAGG                   720

TGCTGCTGCC AACAAGGATA TGTTTGGTTC TGTTTCACCT                   760

TTGGATGATC CAGTTCTCAA TGATGTGGCT AAGAAATACG                   800

GAAAGAGCGT GGCACAAATC TGTCTGAGGT GGGGAATTCA                   840

GAGGAAAACA GCAGTGATTC CAAAATCATC GAAAATTCAG                   880

CGATTGAAAG AGAATTTGGA GGTTCTTGAA TTCCAGCTGA                   920

GCGATGAAGA CATGCAGCTC ATCTACAGTA TCGACAGGAA                   960

GTATCGTACC AGTCTACCTT CCAAGACTTG GGGCTTAGAC                  1000

GTGTATGCAT AAGCGTGCCA TTCAAAAACC TTCGAATTGC                  1040

TGCCTCCGCA ACTTCTTCCA AGGCTGTTCA ACGGAAGCGA                  1080

AATGGAAACT ATCGTGAATC TTACTTACAA TAAACTGAGC                  1120

TTCATATAAT TTTCCAGAAG CTCATCTATC TGCTAGTTTG                  1160

AAAACTTCAT TATTCGCCCT TTGCATTAGG CCTTGCAAAG                  1200

GAAAATATAA TAAACGGCCC TTGTATTTTT TTTGGTACTT                  1240

AATAAATGAG TTATTAAAG                                         1259
```

(2) INFORMATION FOR SEQ ID NO:4:

(i) SEQUENCE CHARACTERISTICS:
        (A) LENGTH: 310
        (B) TYPE: Amino Acid
        (C) STRANDEDNESS: Single
        (D) TOPOLOGY: Linear (ii) MOLECULE TYPE:
        (A) DESCRIPTION:

(iii) HYPOTHETICAL: No (iv) ANTI-SENSE: No (vi) ORIGINAL SOURCE:
        (A) ORGANISM: apple (vii) IMMEDIATE SOURCE:
        (A) LIBRARY: N/A (xi) SEQUENCE DESCRIPTION: SEQ ID NO: 4:

```
Met Ser Thr Val Thr Leu Ser Ser Gly Tyr Glu Met Pro Val Ile
                 5                  10                  15

Gly Leu Gly Leu Trp Arg Leu Glu Lys Asp Glu Leu Lys Glu Val
                20                  25                  30

Ile Leu Asn Ala Ile Lys Ile Gly Tyr Arg His Phe Asp Cys Ala
                35                  40                  45

Ala His Tyr Lys Ser Glu Ala Asp Val Gly Glu Ala Leu Ala Glu
                50                  55                  60

Ala Phe Lys Thr Gly Leu Val Lys Arg Glu Glu Leu Phe Ile Thr
                65                  70                  75

Thr Lys Ile Trp Asn Ser Asp His Gly His Val Val Glu Ala Cys
                80                  85                  90

Lys Asn Ser Leu Glu Lys Leu Gln Ile Asp Tyr Leu Asp Leu Tyr
                95                 100                 105

Leu Val His Tyr Pro Met Pro Thr Lys His Asn Ala Ile Gly Lys
               110                 115                 120

Thr Ala Ser Leu Leu Gly Glu Asp Lys Val Leu Asp Ile Asp Val
               125                 130                 135

Thr Ile Ser Leu Gln Gln Thr Trp Glu Gly Met Glu Lys Thr Val
               140                 145                 150

Ser Leu Gly Leu Val Arg Ser Ile Gly Leu Ser Asn Tyr Glu Leu
               155                 160                 165

Phe Leu Thr Arg Asp Cys Leu Ala Tyr Ser Lys Ile Lys Pro Ala
               170                 175                 180

Val Ser Gln Phe Glu Thr His Pro Tyr Phe Gln Arg Asp Ser Leu
               185                 190                 195

Val Lys Phe Cys Met Lys His Gly Val Leu Pro Thr Ala His Thr
               200                 205                 210

Pro Leu Gly Gly Ala Ala Ala Asn Lys Asp Met Phe Gly Ser Val
               215                 220                 225

Ser Pro Leu Asp Asp Pro Val Leu Asn Asp Val Ala Lys Lys Tyr
               230                 235                 240

Gly Lys Ser Val Ala Gln Ile Cys Leu Arg Trp Gly Ile Gln Arg
               245                 250                 255

Lys Thr Ala Val Ile Pro Lys Ser Ser Lys Ile Gln Arg Leu Lys
               260                 265                 270
```

```
                                -continued

Glu Asn Leu Glu Val Leu Glu Phe Gln Leu Ser Asp Glu Asp Met
                275                 280                 285

Gln Leu Ile Tyr Ser Ile Asp Arg Lys Tyr Arg Thr Ser Leu Pro
                290                 295                 300

Ser Lys Thr Trp Gly Leu Asp Val Tyr Ala
                305                 310
```